United States Patent
Neuland et al.

(10) Patent No.: US 8,616,101 B2
(45) Date of Patent: Dec. 31, 2013

(54) PROCESS AND DEVICE FOR MANUFACTURING A PRODUCT FROM STRIP TAPE, ESPECIALLY FOR MANUFACTURING A MEDICINAL AND/OR ACTIVE SUBSTANCE-CONTAINING PRODUCT AS WELL AS FILLABLE CONTAINERS OR SEALED-MARGIN BAGS

(75) Inventors: Detlev Neuland, Coldwell, NJ (US); Wolfgang Schafer, Ledgewood, NJ (US); Hans-Rainer Hoffmann, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 11/511,213

(22) Filed: Aug. 29, 2006

(65) Prior Publication Data

US 2006/0288834 A1    Dec. 28, 2006

Related U.S. Application Data

(62) Division of application No. 09/980,199, filed as application No. PCT/EP00/04970 on May 31, 2000, now Pat. No. 7,114,422.

(30) Foreign Application Priority Data

Jun. 2, 1999 (DE) ................... 199 25 339

(51) Int. Cl.
*B26D 7/06* (2006.01)
*B26D 3/00* (2006.01)
*B26D 1/22* (2006.01)

(52) U.S. Cl.
USPC ............... 83/86; 83/100; 83/152; 83/425.3; 83/402; 83/407; 226/95; 226/196.1; 270/52.08; 270/58.12; 242/615.12; 242/525.6

(58) Field of Classification Search
USPC ............. 83/98, 100, 156, 402, 407, 659, 676, 83/13, 505, 25, 29, 508.3, 86, 88, 152, 83/425.3, 422; 226/196.1, 195, 95, 7, 226/97.1; 242/615.12, 615.21, 615.11, 566, 242/615.2, 615, 530.2, 525.6; 270/52.08, 270/52.09, 58.31, 58.12, 58.01
See application file for complete search history.

(56) References Cited

U.S. PATENT DOCUMENTS

| | | | | |
|---|---|---|---|---|
| 44,249 | A | * | 9/1864 | Wortendyke ................. 242/530 |
| 1,790,559 | A | | 1/1931 | Swift, Jr. |

(Continued)

FOREIGN PATENT DOCUMENTS

| | | |
|---|---|---|
| DE | 211 962 C | 7/1909 |
| DE | 27 09 211 A | 9/1978 |

(Continued)

OTHER PUBLICATIONS

Patent Abstract of Japan, vol. 010, No. 375 (M-545), Dec. 13, 1986.

(Continued)

*Primary Examiner* — Laura M Lee
(74) *Attorney, Agent, or Firm* — R. S. Lombard; K. Bach

(57) ABSTRACT

A device for manufacturing a product from strip tape includes a roll that draws off and separates a web of material. The web of material is severed into individual strips in cooperation with a multiple circular knife roll. A vacuum conveyor channel is associated with each strip. The vacuum conveyor channel is designed such that each strip is turned on its way to the channel or through the channel by about 90°. The end of the vacuum conveyor channel brings the strips together at one site to form a unit and at that site there are provided a guide and a transport device for the further transport to conversion equipment.

11 Claims, 3 Drawing Sheets

(56) References Cited

U.S. PATENT DOCUMENTS

| | | | |
|---|---|---|---|
| 1,980,400 A | 11/1934 | Grupe | |
| 2,214,593 A * | 9/1940 | Pittaluga et al. | 83/29 |
| 2,293,178 A | 8/1942 | Stocker | |
| 2,332,544 A | 10/1943 | Winkler et al. | |
| 2,506,053 A * | 5/1950 | Zuckerman | 270/18 |
| 2,645,270 A * | 7/1953 | Speed et al. | 156/159 |
| 2,649,035 A * | 8/1953 | Cloud | 493/278 |
| 2,692,736 A * | 10/1954 | Hanley | 242/548.2 |
| 2,717,037 A * | 9/1955 | Goodwillie | 242/525.6 |
| 2,766,950 A * | 10/1956 | Speed et al. | 242/525 |
| 2,821,383 A * | 1/1958 | Clemens | 270/52.08 |
| 2,862,837 A | 12/1958 | Brennan | |
| 3,192,845 A | 7/1965 | Schmidt | |
| 3,411,728 A | 11/1968 | Hall et al. | |
| 3,479,024 A * | 11/1969 | Olson et al. | 270/52.09 |
| 3,556,509 A | 1/1971 | Crum | |
| 3,645,433 A * | 2/1972 | Lucas et al. | 226/190 |
| 3,679,116 A * | 7/1972 | Hamlin et al. | 242/615.12 |
| 3,695,131 A * | 10/1972 | Zimmermann | 83/56 |
| 3,756,527 A | 9/1973 | Collins et al. | |
| 3,850,358 A * | 11/1974 | Nettles | 242/615.11 |
| 3,881,230 A * | 5/1975 | Arnold et al. | 28/263 |
| 3,900,574 A * | 8/1975 | Warwick | 426/274 |
| 4,113,247 A | 9/1978 | Phillips | |
| 4,168,643 A | 9/1979 | Takimoto et al. | |
| 4,349,531 A | 9/1982 | Mlodozeniec et al. | |
| 4,410,122 A * | 10/1983 | Frye et al. | 242/615.2 |
| 4,412,639 A * | 11/1983 | Caletti | 242/615.21 |
| 4,554,716 A * | 11/1985 | Nunn | 28/263 |
| 4,556,441 A | 12/1985 | Faasse, Jr. | |
| 4,572,450 A * | 2/1986 | Lindquist | 242/524.1 |
| 4,666,441 A | 5/1987 | Andriola et al. | |
| 4,693,784 A | 9/1987 | Aula et al. | |
| 4,939,888 A | 7/1990 | Katz et al. | |
| 4,989,487 A | 2/1991 | Staley | |
| 5,172,621 A | 12/1992 | Tacchi et al. | |
| 5,190,233 A * | 3/1993 | Nelson et al. | 242/526 |
| 5,193,423 A | 3/1993 | Bakker | |
| 5,224,405 A | 7/1993 | Pohjola | |
| 5,273,196 A * | 12/1993 | Kubo et al. | 226/97.1 |
| 5,315,461 A * | 5/1994 | Todd | 360/90 |
| 5,374,042 A | 12/1994 | Ring | |
| 5,487,512 A * | 1/1996 | Nojiri et al. | 242/471 |
| 5,499,776 A * | 3/1996 | Nojiri et al. | 242/178 |
| 5,571,361 A | 11/1996 | Stuerzel | |
| 5,794,500 A * | 8/1998 | Long et al. | 83/22 |
| 5,842,664 A * | 12/1998 | Åkerlund | 242/526.3 |
| 5,904,312 A * | 5/1999 | Hinz et al. | 242/525 |
| 6,786,449 B2 * | 9/2004 | Marcle-Geler et al. | 242/615.12 |
| 7,028,940 B2 * | 4/2006 | McNeil et al. | 242/420.6 |
| 7,137,539 B2 * | 11/2006 | Jackson | 225/2 |
| 7,225,527 B2 * | 6/2007 | Kobayashi et al. | 29/603.16 |
| 7,255,302 B2 * | 8/2007 | Shearer et al. | 242/615.21 |
| 7,422,132 B2 * | 9/2008 | Laitio | 226/97.3 |
| 2004/0076799 A1 * | 4/2004 | Schafer et al. | 428/156 |

FOREIGN PATENT DOCUMENTS

| | | | |
|---|---|---|---|
| EP | 0 822 155 | | 2/1998 |
| EP | 0 848 937 A | | 6/1998 |
| GB | 1030369 | * | 5/1966 |
| JP | 63-012567 A | | 6/1988 |

OTHER PUBLICATIONS

Patent Abstract of Japan, vol. 012, No. 208 (M-709), Jun. 15, 1988.

* cited by examiner

PROCESS AND DEVICE FOR MANUFACTURING A PRODUCT FROM STRIP TAPE, ESPECIALLY FOR MANUFACTURING A MEDICINAL AND/OR ACTIVE SUBSTANCE-CONTAINING PRODUCT AS WELL AS FILLABLE CONTAINERS OR SEALED-MARGIN BAGS

CROSS-REFERENCE TO RELATED APPLICATIONS

This nonprovisional application is a Divisional of U.S. application Ser. No. 09/980,199 filed on Mar. 8, 2002 now U.S. No. 7,114,422, which was filed as International Application No. PCT/EP00/04970 on May 31, 2000 and claims priority under 35 U.S.C. §119(a) on Patent Application No. 19925339.0, filed in Germany on Jun. 2, 1999, the entirety of which is incorporated herein by reference.

BACKGROUND OF THE INVENTION

The invention relates to a process for manufacturing a product from strip tape, especially a medicinal and/or active substance-containing product such as, for example, dermal or transdermal patches or another administration form, for example for oral application, as well as fillable containers or sealed-margin bags, in which process there is used as starting material a broad, active agent-containing web of material, for instance of sheet-like materials and, in particular, of active substance-containing sheeting or sheet-like active substance, said process comprising at least two of the following steps:

separating the broad web of material into individual, narrow strips and, if necessary, winding the strips in individual coils or jointly twisting the strips;

unwinding individual coils or pairs of coils, as required, and assembling at least two strips at a time to form a strip web, or unwinding the strip web wound up from individual strips;

processing the web of material to form a product made-up of strip tape; and performing final process steps as, for instance, manufacturing the final product, forming the final application form, laminating the carrier material, segregating, packaging etc.

For manufacturing the above-mentioned products, strip tape consisting of a plurality of individual strips is used. This tape is made by separating a coil of the starting material into individual strips, said coil having a width resulting from the number of strips multiplied by, the width of the strips plus edge trimming. Typically, the resultant strips are wound on reels and are jointly unwound in the number as required and assembled to form webs of material having at least two layers. The manufacture of the stock reels is very labor-intensive, as is the winding and unwinding of the individual strips. It is possible, here, that the material—which may be an active substance-containing material or a medicinal substance—is stretched impermissibly, with the unavoidable elongation of the material having a negative effect on the dosing accuracy of the medicinal substance.

SUMMARY OF THE INVENTION

It is the object of the present invention to provide a process and a device suitable for carrying out said process which overcome the aforementioned disadvantages, difficulties and technical limitations, and, in particular, enable the manufacture of a strip tape product, especially preferred an active substance-containing product, at reduced expenditure in respect of work and costs and without disadvantageous elongation of the material.

To achieve this object in a process of the kind mentioned at the outset, it is proposed according to the invention:

that a roll of material with a broad web of the starting material be mounted, loosely rotatable, on a take-up mandrel;

that the web of material be drawn, in its entire width and without subjecting the material to tensile stress, from the roll of material by means of a vacuum roll, or a device comprising two rolls, which unwinds the material gently from the material roll with one of the rolls simultaneously serving as a counter support to the cutting knifes; the material being separated in the process into individual strips in the negative pressure zone of the vacuum roll by rolling a multiple circular knife roll;

that at the end of the negative pressure zone of the vacuum roll or of the pair of rolls, each strip be drawn from the said vacuum roll or pair of rolls and be introduced in a take-up channel and continuously conveyed therein my means of negative pressure;

that in the process each strip is turned on its way to the channel or through the channel by about 90°; and that at the end of the channels the strips be led one upon the other, at least two at a time, and thereafter conveyed in a, preferably open, groove for further processing under completion to form the final product, to a conversion equipment where the products are finished.

One embodiment of the process provides that for drawing the web of material and separating it into strips in cooperation with the multiple circular knife roll, there is used instead of a vacuum roll, a smooth stripping roll cooperating in a zone where the web of material travels around the roll with a pressure roll and a guide roll.

A device for the manufacture according to the present invention of a product from strip tape, especially of a medicinal and/or active substance-containing product such as, for example, a dermal or transdermal patch or another administration form, for example for oral application, as well as fillable containers or sealed-margin bags, especially for carrying out the process according to the invention, is characterized in that:

as a means for drawing off and separating the web of material a vacuum roll is provided, in whose web-travelling zone the web of material, held by the negative pressure, can be severed into individual strips in cooperation with the multiple circular knife roll;

to each strip there is associated a vacuum conveyor channel which is designed such that each strip is turned on its way to the channel or through the channel by about 90°; and the ends of all the take-up channels 12 are brought together at one site to form a unit and that at that site there are provided guide means and transport means for the further transport to a conversion equipment.

One embodiment of the device according to the invention provides that as means for drawing the web of material and for transport during the separation into strips in cooperation with the multiple circular knife roll, there is provided instead of a vacuum roll, a smooth stripping roll arranged in a zone where the web of material travels around the roll and adapted to cooperate with a pressure roll and a guide roll.

The process according to the invention and the device provided for carrying out the same overcome the aforementioned disadvantages, difficulties and technical limitations of the prior art and, in particular, enable the manufacture of medicinal and/or active substance-containing products at reduced expenditure in terms of work and costs without disadvantageous elongation of the starting material.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
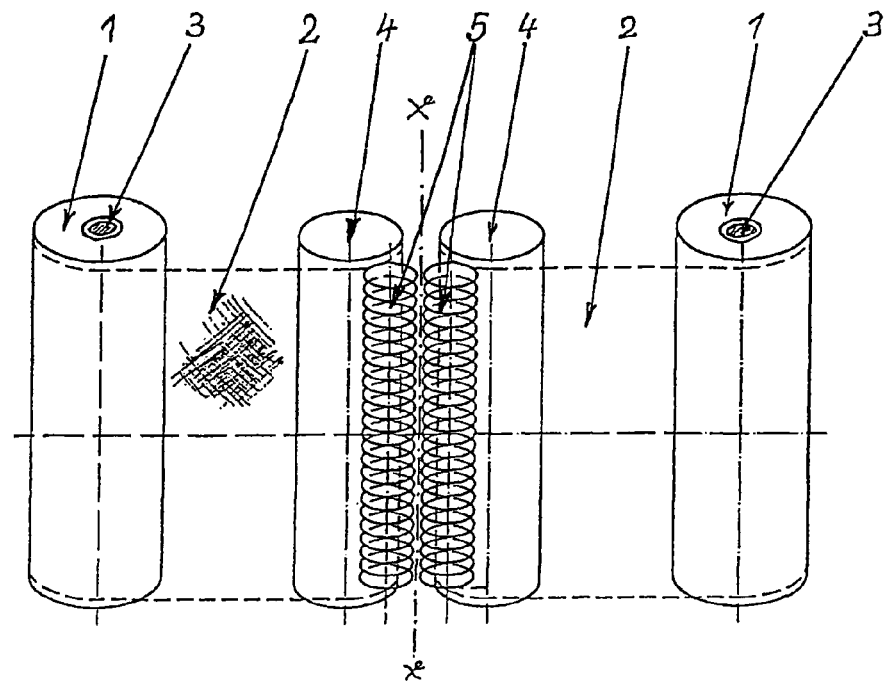
FIG. 1 is a side view of the device according to an embodiment of the present invention.

The part of the device represented in FIG. 1 shows rolls of material 1 with a web 2 of the starting material in a duplicate arrangement on both sides of a plane of symmetry x—x, said rolls 1 being mounted on take-up mandrels 3, as well as a duplicate arrangement of vacuum rolls 4, and circular knife rolls 5 rolling on said vacuum rolls 4 and the web of material 2 and having a plurality of circular knifes disposed parallel thereto.

Figure 2:
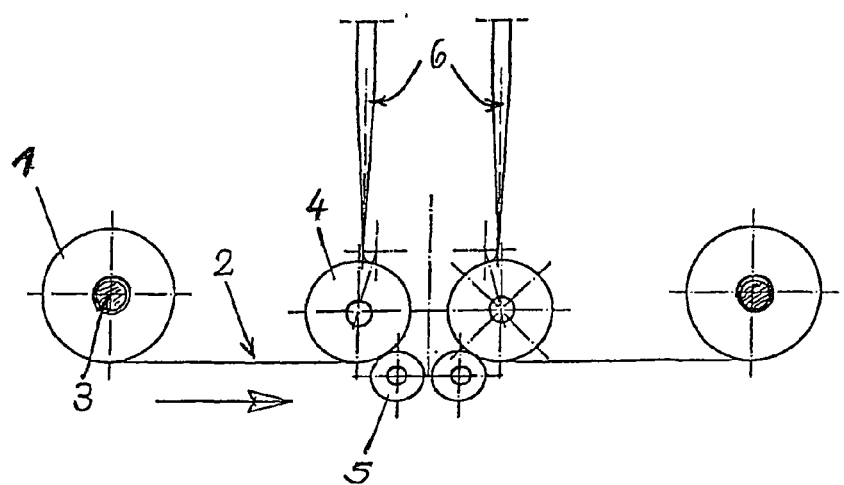
FIG. 2 is a plan view of the device according to FIG. 1.

The same device is shown in FIG. 2 in plan view, with rolls of material 1, mounting mandrel 3, the material web 2, which can be uncoiled, vacuum rolls 4, circular knife rolls 5, and strips of material 6 cut from the web 2 and running off the said circular knife rolls 5 at the end of the vacuum zone.

Figure 3:
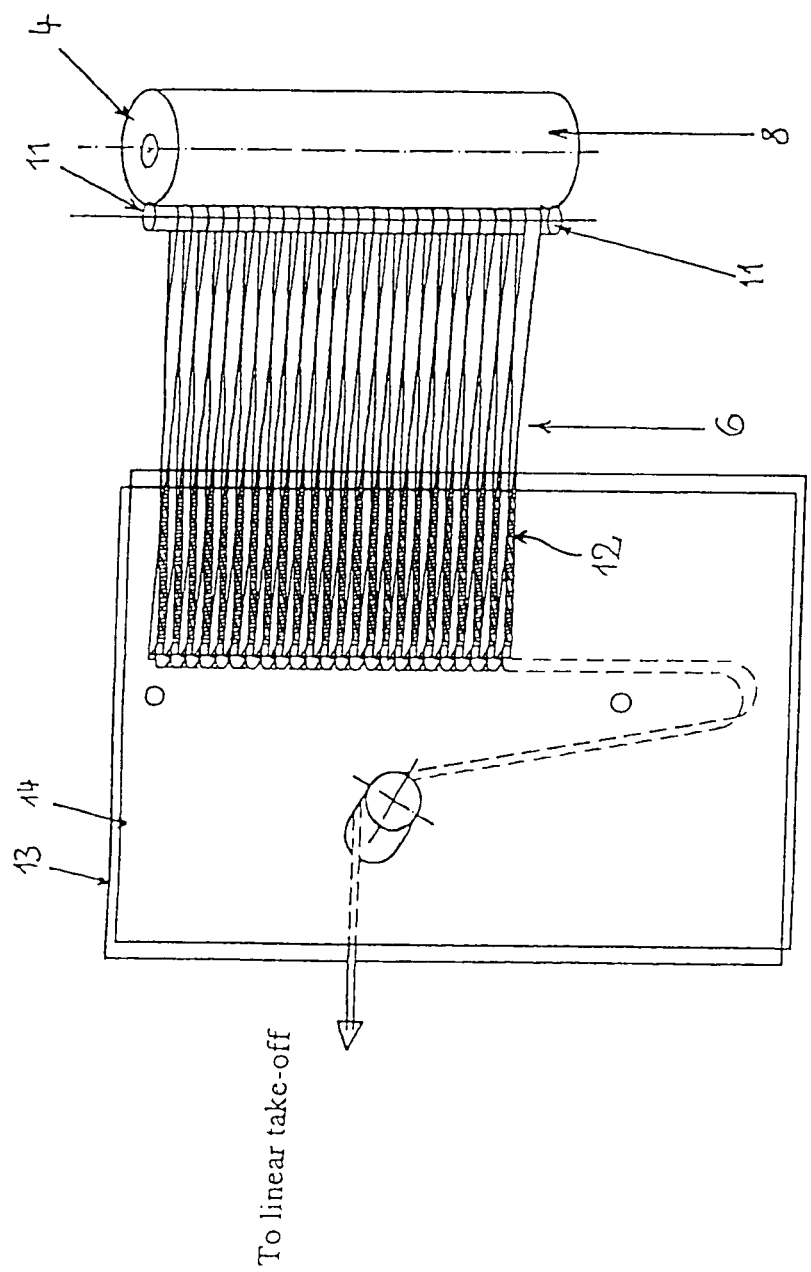
FIG. 3 is a partial view of the device with vacuum transport channels disposed at the end of the device.
Figure 4:
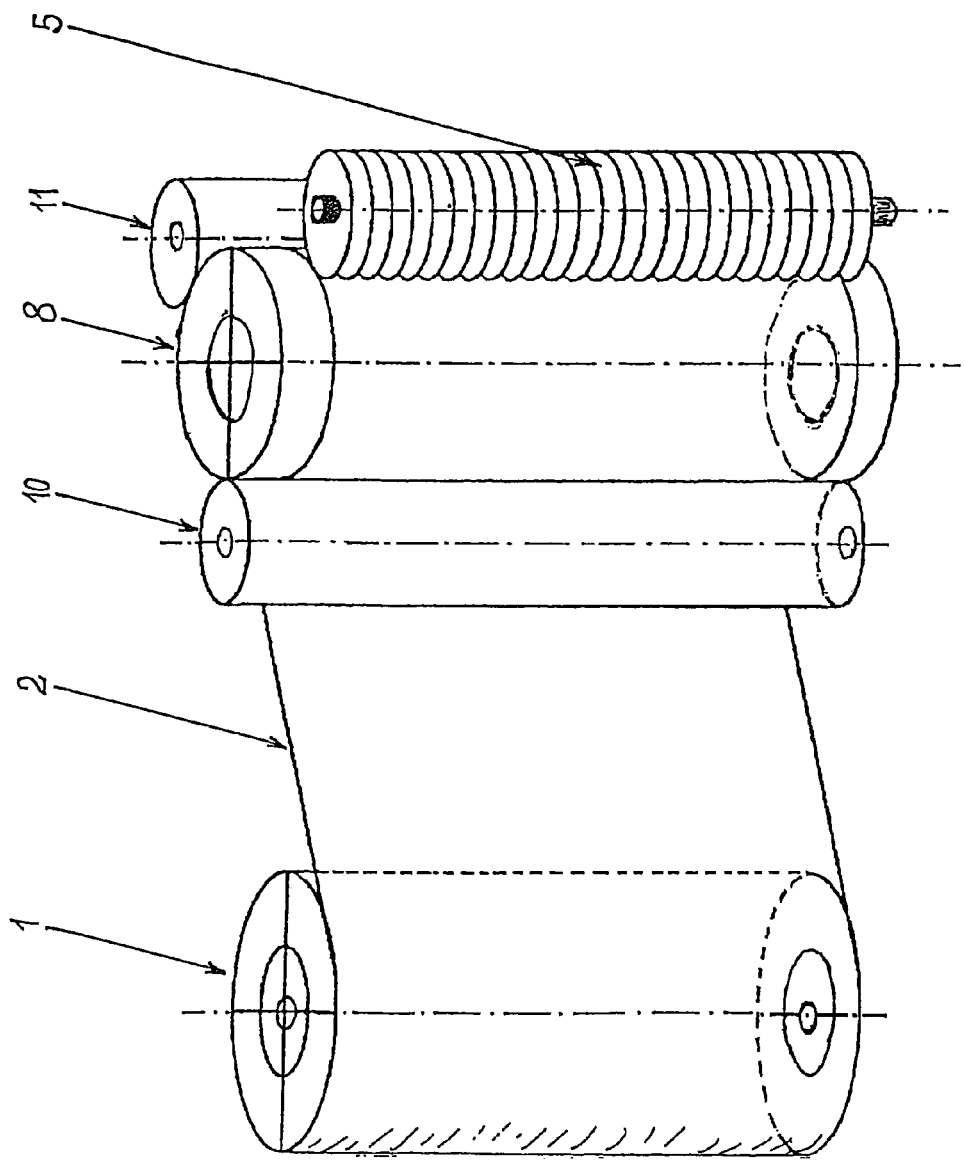
FIG. 4 is a view of the device in which a smooth stripping roll is provided instead of a vacuum roll.

FIG. 3 shows, in part in side view and in part in plan view, a vacuum roll 4. However, this may also be a stripping roll 8 aided by a guide roll 11, from which strips 6, cut by a circular knife roll (not shown), are transported in the width of the original web of material 2. For linear take-off of a plurality of strips 6 there are provided vacuum conveyor channels or take-up channels 12, each formed, for example, between two cover plates 13 and 14. Finally, FIG. 4 shows an alternative embodiment of the device wherein instead of a vacuum roll, a smooth stripping roll 8 arranged in a zone in which the material web 2 travels around the roll and adapted to cooperate with a pressure roll 10 and a guide roll 11 is provided as a means for drawing the material web 2 and for transport thereof during separation of the web of material in strips 6 in cooperation with a multiple circular knife roll 5 .

The process and device are uncomplicated, reduce the expenditure of work and costs required heretofore, and enable the manufacture from strip tape of medicinal and/or active substance-containing products of various design, or of fillable containers or sealed-margin bags, while avoiding a disadvantageous elongation of the material, and, in particular, using a starting material in the form of sheet-like material, preferably a sheet-like active substance-containing administration form.

The present invention thus constitutes an optimal solution to the task presented at the outset.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for manufacturing a medicinal or active substance-containing product from strip tape, comprising:
a pair of oppositely disposed with respect to a plane of symmetry x-x broad web medicinal or active-substance containing material rolls, said broad web material rolls for drawing off and separating a web of material, each of said broad web material rolls having the broad webs of material loosely rotatable on a take up mandrel for preventing excessive stretching of the broad web material, each of said broad web material rolls in operative arrangement with a vacuum roll adapted to draw off by negative pressure and separate the web of material or a smooth stripping roll adapted to cooperate with a pressure roll and a guide roll to draw off and separate the web of material in a web traveling zone; a pair of multiple circular knife rolls each disposed coaxially parallel to and proximate with the plane of symmetry x-x and each disposed and associated in rolling cutting relationship with one of the vacuum rolls or smooth stripping rolls for cutting each of said broad web carrying material rolls into a plurality of individual strips simultaneously, each of the multiple circular knife rolls being counter supported by its associated vacuum roll or its associated smooth stripping roll,
a pair of vacuum conveyors each operatively arranged to receive one of the broad web carrying material rolls that is in the form of a plurality of individual strips, each vacuum conveyor having a plurality of channels for receiving and conveying an individual strip formed between two cover plates, each vacuum conveyor channel for causing each individual strip to be rotated about 90° around each strip's longitudinal axis from a first orientation to a second orientation on its way to the channel or through the channel with the longitudinal axis not changing direction, the plurality of channels of each said vacuum conveyors for bringing the individual strips associated therewith into stacked relationship with respect to one another to form the strip tape.

2. The device according to claim 1, wherein the strip tape is for a medicinal and/or active substance-containing product.

3. The device according to claim 1, wherein the strip tape is for a dermal or transdermal patch.

4. The device according to claim 1, wherein the strip tape is for an oral application.

5. The device according to claim 1, wherein the strip tape is for fillable containers or sealed-margin bags.

6. The device according to claim 1, wherein said cover plates are arranged parallel to one another.

7. The device according to claim 1, wherein said smooth stripping roll cooperates with said pressure roll, said guide roll and said counter supported multiple circular knife roll.

8. The device according to claim 1, wherein each of said vacuum conveyor channels has an entry opening for introducing said associated individual strip.

9. The device according to claim 8, wherein said smooth stripping roll cooperates with said guide roll, said guide roll being arranged opposite to and at a distance from said entry opening of said vacuum conveyor channels.

10. The device according to claim 1, wherein the vacuum conveyor channels are for rotating each strip from a first conveyance plane to a second conveyance plane, the second conveyance plane being substantially perpendicular to the first conveyance plane.

11. The device according to claim 1, wherein each strip is continuously conveyed in its associated said vacuum conveyor channel by means of negative pressure.

\* \* \* \* \*